US005310892A

United States Patent [19]

Aris et al.

[11] Patent Number: 5,310,892

[45] Date of Patent: May 10, 1994

[54] NUCLEIC ACID SEQUENCE WHICH CODES FOR AND EXPRESSES HUMAN FIBRILLARIN AND USES THEREOF

[75] Inventors: John Aris; Günter Blobel, both of New York, N.Y.

[73] Assignee: The Rockefeller University, New York, N.Y.

[21] Appl. No.: 626,680

[22] Filed: Dec. 10, 1990

[51] Int. Cl.[5] ...................... C07H 21/04; C12N 15/12

[52] U.S. Cl. .................................. 536/23.5; 435/69.1; 435/69.2; 435/320.1; 530/350; 530/358; 536/24.31

[58] Field of Search .................. 530/350, 358; 536/23, 536/23.5, 24.31; 435/69.1, 69.2, 320, 320.1

[56] References Cited

PUBLICATIONS

Schimmang, T. et al., EMBO J. 8(13):4015–4024. (Dec. 20, 1989).

LaPeyre, et al. Mol. Cell Biol. 10(1):430–4. (Jan. 1990).

R. A. Heller-Harrison et al. Biochemistry 28:9053–58 (1989) "Cloning and Characterization of a cDNA Encoding the B-Subunit of Human Casein Kinase II."

Ruben Henriquez, thesis (1990), "Molecular Cloning and Characterization of the Yeast Gene Encoding Fibrillarin a Major Nucleolar Protein". pp. 39, 41, 55, 56, 59.

J. Aris, et al. Jul. 1988. J. Cell. Biol. 107:17–31.

Ochs et al., Biol. Cell 54: 123–134 (1985).

Lischwe et al., J. Biol. Chem. 260(26): 14304–14310 (1985).

Reimer et al., Arth. & Rheumn. 30(7): 793–800 (Jul. 1987).

Henriquez et al., J. Biol. Chem. 265(4): 2209–2115 (Feb. 5, 1990).

*Primary Examiner*—Christine M. Nucker
*Assistant Examiner*—T. Cunningham
*Attorney, Agent, or Firm*—Felfe & Lynch

[57] ABSTRACT

Substantially pure nucleic acid sequences coding for human fibrillarin have been identified and isolated. The isolated material is used to generate the protein in vitro, which is then used to identify autoimmune antibodies in patients suffering from scleroderma.

10 Claims, 3 Drawing Sheets

FIG. 1

-28 CCCGGAGCCGCACAAACCAGGGCTCGCCATG AAG CCA GGA TTC AGT CCC CGT GGG GGT GGC TTT GGC GGC CGA GGG GGC TTT GGT GAC
1 MET LYS PRO GLY PHE SER PRO ARG GLY GLY GLY PHE GLY GLY ARG GLY GLY PHE GLY ASP

61 CGT GGT GGT CGT GGA GGC CGA GGG GGC TTT GGC GGG GGC CGA GGT CGA GGC GGA GGC TTT AGA GGT CGT GGA CGA GGA GGA
21 ARG GLY GLY ARG GLY GLY ARG GLY GLY PHE GLY GLY GLY ARG GLY ARG GLY GLY GLY PHE ARG GLY ARG GLY ARG GLY GLY

142 GGT GGA GGC GGC GGC GGC GGT GGA GGA GGA GGA AGA GGT GGT GGA GGC TTC CAT TCT GGT GGC AAC CGG GGT CGT GGT CGG
48 GLY GLY GLY GLY GLY GLY GLY GLY GLY GLY GLY ARG GLY GLY GLY GLY PHE HIS SER GLY GLY ASN ARG GLY ARG GLY ARG

223 GGA GGA AAA AGA GGA AAC CAG TCG GGG AAG AAT GTG ATG GTG GAG CCG CAT CGG CAT GAG GGT GTC TTC ATT TGT CGA GGA
75 GLY GLY LYS ARG GLY ASN GLN SER GLY LYS ASN VAL MET VAL GLU PRO HIS ARG HIS GLU GLY VAL PHE ILE CYS ARG GLY

304 AAG GAA GAT GCA CTG GTC ACC AAG AAC CTG GTC CCT GGG GAA TCA GTT TAT GGA GAG AAG AGA GTC TCG ATT TCG GAA GGA
102 LYS GLU ASP ALA LEU VAL THR LYS ASN LEU VAL PRO GLY GLU SER VAL TYR GLY GLU LYS ARG VAL SER ILE SER GLU GLY

385 GAT GAC AAA TTT GAG TAC CGA GCC TGG AAC CCC TTC CGC TCC AAG CTA GCA GCA GCA ATC CTG GGT GGT GTG GAC CAG ATC
129 ASP ASP LYS PHE GLU TYR ARG ALA TRP ASN PRO PHE ARG SER LYS LEU ALA ALA ALA ILE LEU GLY GLY VAL ASP GLN ILE

466 CAC ATC AAA CCG GGG GCT AAG GTT CTC TAC CTC GGG GCT GCC TCG GGC ACC ACG GTC TCC CAT GTC TCT GAC ATC GTT GGT
156 HIS ILE LYS PRO GLY ALA LYS VAL LEU TYR LEU GLY ALA ALA SER GLY THR THR VAL SER HIS VAL SER ASP ILE VAL GLY

547 CCG GAT GGT CTA GTC TAT GCA GTC GAG TTC TCC CAC CGC TCT GGC CGT GAC CTC ATT AAC TTG GCC AAG AAG AGG ACC AAC
183 PRO ASP GLY LEU VAL TYR ALA VAL GLU PHE SER HIS ARG SER GLY ARG ASP LEU ILE ASN LEU ALA LYS LYS ARG THR ASN

628 ATC ATT CCT GTG ATC GAG GAT GCT CGA CAC CCA CAC AAA TAC CGC ATG CTC ATC GCA ATG GTG GAT GTG ATC TTT GCT GAT
210 ILE ILE PRO VAL ILE GLU ASP ALA ARG HIS PRO HIS LYS TYR ARG MET LEU ILE ALA MET VAL ASP VAL ILE PHE ALA ASP

709 GTG GCC CAG CCA GAC CAG ACC CGG ATT GTG GCC CTG AAT GCC CAC ACC TTC CTG CGT AAT GGA GGA CAC TTT GTG ATT TCC
237 VAL ALA GLN PRO ASP GLN THR ARG ILE VAL ALA LEU ASN ALA HIS THR PHE LEU ARG ASN GLY GLY HIS PHE VAL ILE SER

790 ATT AAG GCC AAC TGC ATT GAC TCC ACA GCC TCA GCC GAG GCC GTG TTT GCC TCC GAA GTG AAA AAG ATG CAA CAG GAG AAC
264 ILE LYS ALA ASN CYS ILE ASP SER THR ALA SER ALA GLU ALA VAL PHE ALA SER GLU VAL LYS LYS MET GLN GLN GLU ASN

871 ATG AAG CCG CAG GAG CAG TTG ACC CTT GAG CCA TAT GAA AGA GAC CAT GCC GTG GTC GTG GGA GTG TAC AGG CCA CCC CCC
291 MET LYS PRO GLN GLU GLN LEU THR LEU GLU PRO TYR GLU ARG ASP HIS ALA VAL VAL VAL GLY VAL TYR ARG PRO PRO PRO

952 AAG GTG AAG AAC TGAAGTTCAGCGCTGTCAGGATTGCGAGAGATGTGTGTTGATACTGTTGCACGTGTGTTTTTCTATTAAAAGACTCATCCGTCA$_{30}$ +1076
318 LYS VAL LYS ASN ---

NUCLEIC ACID SEQUENCE WHICH CODES FOR AND EXPRESSES HUMAN FIBRILLARIN AND USES THEREOF

FIELD OF THE INVENTION

This invention refers to recombinant DNA technology and its application to immune diagnosis. More particularly, it refers to the isolation of nucleic acid molecules which code for or express a protein associated with the autoimmune disease scleroderma, and the protein product of transcription and translation of the nucleic acid, human fibrillarin.

BACKGROUND AND PRIOR ART

One of the features of the immune system currently under study is the process by which the immune system "fails", and generates antibodies against so-called "self" antigens in the subject. This phenomenon leads to the development of the so-called autoimmune diseases which include arthritis, rheumatism, some forms of diabetes and the disease under discussion herein, scleroderma.

In the autoimmune diseases studied, one generally finds that the disease can be correlated to an immune response against a normal protein produced by the organism, a particular cell type, etc. The mechanism by which this takes place is under intensive investigation, but for now, most efforts center on the diagnosis of the conditions.

Diagnosis of an autoimmune disease most practically requires identification of antibodies against the particular protein. In theory, this is a very simple concept to understand. In practice it is difficult to provide appropriate diagnostic methodologies. Proteins produced by organisms such as humans are produced in extremely small quantities, and securing amounts of these proteins sufficient even for laboratory, research, involves large scale, difficult purification for vanishingly small yields. For example, purification of the naturally occurring hormone erythropoietin once required processing of 2500 liters of urine to secure a few milligrams of protein. Clearly, this is not an acceptable approach for diagnosis.

Given the developments in DNA technology, one approach to this problem has been to locate and to isolate nucleic acid sequences which code for or express the protein of interest. Again, in theory, the DNA, e.g., is isolated, transfected into host cells, and large quantities of protein produced. In practice, this is not always, and usually is not very simple. Among the issues confronting the investigator are: (i) the number of copies of the gene available, (ii) whether the gene is available in a cell type under consideration, (iii) assuming the gene is available, can it be identified, and (iv) can it be adapted to work in a non-source cell environment.

The issues around (i) and (ii) are self evident, and will not be discussed further. As to (iii), theory says that once one has even a small amount of protein available one secures its amino acid sequence and, using the genetic code, constructs oligonucleotide probes to locate the gene. Again, the practitioner knows that the issues around this theory include the problem of creating a probe that is precisely the right size to locate the desired gene and no other. This is not very easy to solve, and involves a great deal of trial and error.

If nucleic acids expressing or coding the protein of interest from another species are available, again, the theory says that, based on expected homology, one ought to be able to find, e.g., a human gene using the genes or fragments thereof from other species. When the protein of interest possesses a dissimilar sequence, however, this methodology will fail. Regarding (iv), supra, once a clone is isolated, there is no guarantee that it will work outside of its "home" environment.

With respect to the nucleic acids coding for fibrillarin, although proteins and DNA for other species were known, as per Lapeyre et al., Mol. Cell Biol. 10: 430–434 (1990) (Xenopus DNA); Henriquez et al., J. Biol. Chem. 265: 2209–2215 (1990) (yeast DNA), the disclosures of which are incorporated by reference herein, the normal protocols and theoretical considerations did not permit isolation of the human gene, nor the pure protein.

A methodology has been developed, however, which has permitted the inventor to identify and isolate nucleic acid sequences which code for and express human fibrillarin. In addition, it has been found that the isolated nucleic acid sequences will produce human fibrillarin in vitro, eliminating problems which may be encountered in in vivo systems. Finally, the protein itself has been produced and purified in quantities sufficient to permit characterization and use thereof.

These and other aspects of the invention are developed in detail via the disclosure which follows.

BRIEF DESCRIPTION OF THE FIGURES

FIG. 1 depicts the cDNA sequence and amino acid sequence of human fibrillarin.

DETAILED DESCRIPTION OF PREFERRED EMBODIMENT

Example 1

Figure 2:
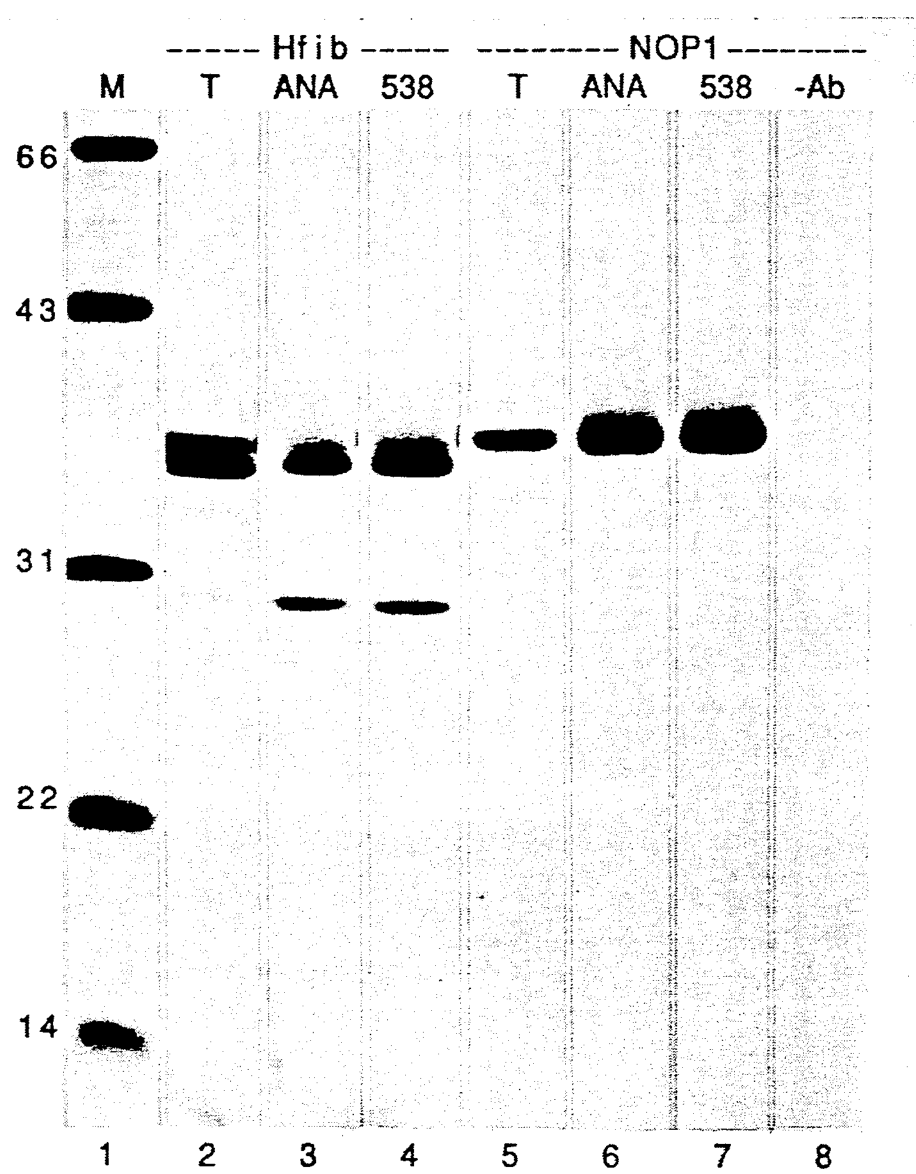
FIG. 2 shows Northern Blot analysis of human and yeast RNA for determination of human fibrillarin mRNA.
Figure 3:
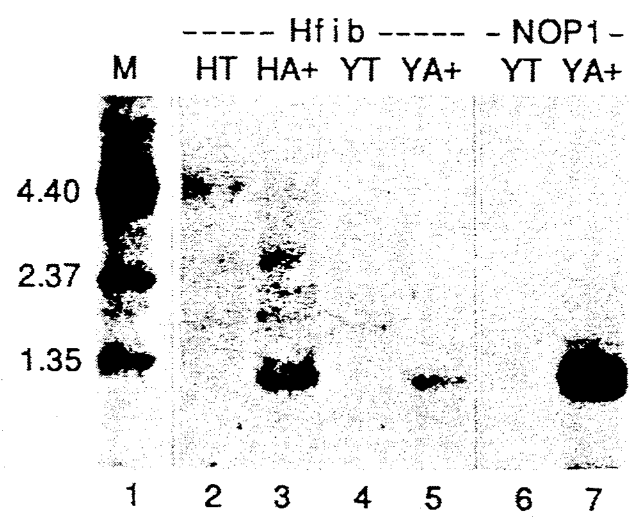
FIG. 3 presents data showing the immunoprecipitation of both human and yeast fibrillarin with autoimmune serum.

This example describes the isolation of cDNA for human fibrillarin.

A total human hepatoma cDNA library (HepG2), once amplified in λ bacteriophage ("λZAP", obtained from Strategene), was used as the starting material. This was probed with DNA probes derived from the yeast *S. cervisae* fibrillarin gene "NOP1", as per Henriquez et al., J. Biol. Chem. 265: 2209–2215 (1990); and the gene from *Xenopus laevis,* referred to as "Xomfib", as described by Lapeyere et al., Mol. Cell Biol. 10: 430–434 (1990). These disclosures, teaching NOP1 and Xomfib, are incorporated by reference herein. To elaborate, the probe from yeast was a 443 bp Bst XI-NdeI restriction fragment, and the frog probe was the 1.19kb AvaI fragment. These were purified by agarose gel electrophoresis and were labeled with $^{32}P$ by random hexamer priming, following Lapeyre, supra, Henriquez, supra, and Feinberg et al., Anal. Biochem. 132: 6–13 (1983). The NOP1 fragment did not include the known G-C rich, repetitive region at the 5'end. The Xomfib clone only included about 50 base pairs of its equivalent region. In experiments not reported herein, initial attempts to isolate the human gene by using yeast derived probes failed. This is attributable to a high degree of false hybridization due to G-C rich regions present in the yeast gene. Probing with frog derived materials was not done, because the same problem was envisioned, due to G-C rich regions in the Xenopus probe.

Each of these two probes was incubated with a set of replica filters, representing about $10^6$ plaques. The hybridization and ensuing washes were carried out under standard methods of low stringency to give a $T_m$ of −35° C. for NOP1, and one of −30° C. for Xomfib, assuming a probe of 100 base pairs, as per Ausubel et al., eds, *Currently Protocols In Molecular Biology (N.Y.*, 1990; Greene Publishing and Wiley—Interscience); Maniatis et al., *Molecular Cloninq, A Laboratory Manual* (Cold Spring Harbor Laboratory, N.Y. 1982). To elaborate, hybridization was carried out at 42° C. Many conditions were identical for the hybridization protocols—i.e., for both NOP1 and XomFib, the hybridization medium contained 25mM $NaPO_4$ (pH 7.5), 25 mM Hepes (pH 7.5), 1 mM EDTA, 0.1% SDS, 1xSSC, 5xDenhardt's solution, and −100 ug/ml of E. coli DNA as a carrier. The probes themselves were in either 10% (NOP1) or 20% (Xomfib) formamide. The DNA templates had been labeled by nick translation, and approximately 50 ng (NOP1) or 110 ng (Xomfib) were used.

With respect to the washing steps used in the experiments, either low stringency or high stringency conditions were used. For NOP1, "low stringency" is defined as requiring 2xSSC at 25° C., and a "high stringency" wash requires 1xSSC at 50° C. For Xomfib, low stringency is the same as NOP1. High stringency conditions call for 0.5x SSC at 50° C.

Seventeen isolates were purified by limiting dilution, and their inserts were retrieved by in vivo excision using R408 helper phage and *Escherichia coli* strain BB-4 to yield pBluescript SK+(Stratagene) plasmids containing inserts. The plasmid retrieved from clone λ20 hybridized under conditions of high stringency in the presence of tetramethylammonium chloride to a degenerate mixture of complementary oligonucleotides based on the aminoterminal sequence MKPGFS of rat fibrillarin. Phage DNA was prepared from λ20 and the insert was ligated into the EcoRI site of pBluescript SK+ to generate the plasmid p20J. Forty-eight bp of untranslated sequence at the 5′ end of the cDNA insert in p20J were removed to generate plasmid p20J2. This was done in order to eliminate a potential problem with an upstream ATG codon out of frame with the correct initiator ATG during the expression of human fibrillarin in the rabbit reticulocyte cell-free system.

EXAMPLE 2

The insert in p20J was sequenced, using standard techniques. This sequencing showed that an ATG codon was out of frame with the initiator sequence. It also permitted observation of a 48 base pair sequence of untranslated nucleotides at the 5′end, which included the out of frame codon. This fragment was excised out of the insert, yielding plasmid p20J2.

The strands of the insert in p20J2 were sequenced using dideoxynucleotide chain termination methodology, including the use of modified T7 polymerase, dGTP and dITP for ambiguous sequences. See Sanger et al., Proc. Natl. Acad. Sci. U.S.A. 74: 5463–5467 (1977); Tabor et al., Proc. Natl. Acad. Sci. U.S.A. 84: 4767–4771 (1987). Sequencing reactions were done using double stranded DNA templates, and synthetic primers 17 bases long. The open reading frame for the clone was determined by comparing it to yeast and frog fibrillarin amino acid sequences.

The clone is found to be 1104 base pairs long. It contains a single long open reading frame, beginning with ATG near one end, as will be seen in sequence id no. 1. The ATG, followed by 15 base pairs encoding MKPGFS, constitutes the site of hybridization of the oligonucleotide probes described supra. In addition, a nucleotide sequence upstream of the ATG, i.e., TCGCC, agrees with the consensus sequence found at most translation sites ($CC^{A}/_{G}CC$; see Kozak, Nucl. Acids Res. 12: 857–872 (1984)).

Analysis of the sequence shows that the amino terminal end, beginning with ATG is identical to 30 of 31 chemically determined amino terminal residues of the rat protein, as described by Lischwe et al., J. Biol. Chem. 260: 14304–14310 (1985). It can be inferred that the ATG at +1 is the initiation codon. The open reading frame extends for 963 base pairs, coding a 321 amino acid protein of putative molecular weight of 33923 kilodaltons. This is pretty much confirmed by experiments described infra. The protein also has a predicted isoelectric point (pI) of about 10. The 5′end of the reading frame is rich in purine nucleosides, with the nucleotides coding for amino acid 6 through 75 showing a G+C content of 70.5%, in contrast to a total content of 57.6%. The reading frame ends with a stop codon, and is followed by an 80 nucleotide 3′untranslated region, and a poly(A)region. The polyadenylation signal ATTAAA in the 3′ flanking region is 13 nucleotides from the poly A tail. In contrast, Xenopus clones show a 3′ flanking sequence with a long, untranslated spacer between termination codon and polyadenylation signal, while in yeast, the polyadenylation signals are within 70 nucleotides of the termination codon.

EXAMPLE 3

Experiments were then carried out to identify human fibrillarin mRNA, and to study cross hybridization with other mRNAs. To do this, first human total and poly(A)RNA from HeLa cells were obtained, following Wozniak et al., J. Cell Biol. 108: 789–795 (1989). Total and poly(A)RNA were Obtained from *S. cervisae*, following Henriquez et al., supra. The samples (5 ug total; 2 ug poly(A)) were electrophoresed in 1% agarose/formaldehyde gel, transferred to nitrocellulose membranes, and treated as per Henriquez, Ausubel and Maniatis, all supra. Either the EcoRI restriction fragment from p20J2 or the genomic EcoRI fragment containing NOP1 were isolated from low melting point agarose gel, and $^{32}P$ labeled as described supra. The NOP1 probe was incubated with the blot under standard conditions as described supra, and washed twice with 0.125xSSC at 55° C. The human blot was placed in −100° C. water, cooled for 5 minutes and exposed to film to verify complete removal of the NOP1 probe. The blot was hybridized to human fibrillarin probe from p20J2 using identical conditions as listed supra, followed by two 1×SSC washes at 25° C.

These experiments revealed an RNA in the poly(A)RNA enriched sample, but not in total human RNA. The size of the RNA is approximately 1.3 kb, as shown in FIG. 1. This size is consistent with the size of human fibrillarin cDNA with a poly A tail.

Using the moderately stringent hybridization conditions described supra, the human fibrillarin DNA probe revealed two cross hybridizing mRNAs. The human probes also weakly detect a human RNA of approximately 2.7kb in the poly A samples. This is probably mRNA for human nucleolin, a nucleic protein of 100 kd which contains a repeated amino acid sequence rich in glycine and arginine near the carboxy terminus, as per Lapeyre et al., Proc. Natl. Acad. Sci. U.S.A. 84: 1472–1476 (1987). In a similar experiment, using Xenopus RNA, a Xenopus fibrillarin cDNA probe cross hybridized to 2.7 kb Xenopus nucleolin mRNA. Also, using yeast samples, the human probe detected a 1.3 kb band found in the poly(A)RNA. Finally, hybridization experiments using the same blot, a yeast fibrillarin (NOP1) probe, and high stringency conditions, showed that the 1.3 kb band is yeast fibrillarin mRNA. Prior work by Henriquez et al., supra showed that yeast fibrillarin mRNA is about 1.3 Kb in size.

Example 4

The identity of the human cDNA clone was confirmed by a second approach, in vitro translation followed by precipitation with autoimmune antiserum.

In these experiments, cell free translation was carried out for one hour at 25° C. in a 50 ul reaction volume containing 20ul rabbit reticulocyte lysate, 100 μCi [$^{35}$S] methionine, 5U RNasin, and ~500 ng mRNA, as per Nicchitta et al., J. Cell Biol. 108: 789–795 (1989). Human or yeast fibrillarin mRNA was prepared by transcription of plasmid p20J2 linearized with BamHI, or plasmid pNOP1-RV, linearized with EcoRI. The latter plasmid was prepared by digesting a clone taught by Henriquez, supra, followed by blunt end ligation following Ausubel, supra. The transcription of the plasmid used 25 ul of p20J2, with T7 RNA polymerase and an RNA transcription kit. The initiation codon ATG is positioned 88 base pairs downstream from a T7 polymerase promoter in the plasmid.

Following translation, 1 ul of translation production was subjected to SDS PAGE on a 12% gel. As analyzed per FIG. 2, the gel migration pattern showed two proteins, migrating as a doublet of approximately 37 and 36 kd. The, electrophoresed samples were then treated with dithiothreitol followed by iodoacetamide, which reduces the amount of the 37 kd band. The 36 kd band agrees with molecular mass for fibrillarin in several mammalian species. See Lischwe et al., J. Biol. Chem. 260: 14304–14310 (1985); Ochs et al., Biol. Cell 54: 123–134 (1985); Reimer et al., Arthritis & Rheumatism 30: 793–800 (1987). When rat liver nucleic fibrillarin was tested on SDS-PAGE, it migrated with a molecular weight of about 36 kd.

Example 5

The cell free translation product of example 4 was then used in precipitation studies. Sera from patients with systemic sclerosis (scleroderma) were incubated with fibrillarin produced supra in the presence of nonionic detergent Triton X-100. Specifically, 50 ul samples of the translation product were diluted with 950 ul of 1% Triton X-100 and 1 mM iodoacetamide in IP buffer (50 mM Tris, pH 7.5, 150 mM $NaN_3$). Following this, 200 ul of diluted translation mixture was combined with 20 ul of anti-nuclear antiserum ("ANA" hereafter), which is equivalent to 1.0 ul of undiluted antiserum, or 0.5 ul of antiserum from a patient with scleroderma, or no antiserum at all. The ANA was used because fibrillarin was originally identified using this type of material. See Ochs et al., Biol. Cell 54: 123–131(1985). The patient antiserum had previously been tested and was shown to recognize yeast fibrillarin with high specificity.

After incubation on ice for two hours, the samples were centrifuged for 5 minutes at 12,000 g at 4° C. The supernatant was transferred to a microfuge test tube containing 15 ul of protein G Sepharose which had previously been washed with IP buffer plus 1% Triton X-100. This was incubated for 1 hour at approximately 25° C. with gentle mixing. The sepharose was collected by brief centrifuging, and washed at approximately 25° C., sequentially, with IP buffer plus 1% Triton X-100, and 2M urea, IP buffer plus the detergent, and 10 volumes of water. The samples were then prepared for electrophoresis by treatment with 50 mM DTT by boiling for 3 minutes, followed by addition of one tenth volume of fresh 1M iodoacetamide. Samples were analyzed by SDS-PAGE, as above. Gels were treated for fluorography after running.

The results of these experiments are shown in FIG. 2. The gel analysis shows a 36 kd protein, the human fibrillarin, and a 30 kd protein. This protein may be the translation product of the fibrillarin gene, starting at Met-87.

In additional experiments the antisera used herein precipitated yeast fibrillarin produced in vitro, which migrates at 38 kd, also shown in FIG. 2. Also, nonspecific association of fibrillarin with protein G-Sepharose did not occur.

It was also observed that immunoprecipitation was abolished by boiling prior to dilution, presumably because of denaturation of the protein.

Comparison of the human protein amino acid sequence with the Xenopus and Saccharomyces proteins shows that there are approximately 90 amino acids that resemble the so-called "RNA-binding domain" involved in, and possibly essential for interaction with RNA or single strand DNA in many RNA binding proteins. See, e.g., Query et al., Cell 57: 89–101 (1989); Bandziulio et al., Genes Dev 3: 431–437 (1989); Mattaj et al., Cell 57: 1–3 (1989). The interaction between human fibrillarin and small nucleolar RNAs ("snos"), may be mediated by these sequences.

Human and Xenopus fibrillarin show 90% homology and are 81% identical. Comparable figures for yeast are: 82% conservation, 67% identical.

The primary structures of these molecules may be compared further. The human protein begins with a glycine/arginine rich domain, leading to 20.2 mol % Gly and 4.2 mol % Arg in the molecule. This domain, at the N-terminus, is repetitive and similar to Xenopus and yeast, which shows a repeat (4x) having only 3 amino acid differences. The human sequence does not show precise repetition of duplicated elements, but does show one stretch of 17 glycines interrupted by a single arginine. The ending of the domain is somewhat ambiguous, occurring near Lys-77 and Lys-84, whereas in Xenopus and yeast it is always at Lys-85. The human domain does contain one acidic residue, Asp-20, bounded by 4 residues of sequence GDRGG. When Asp occurs at the end terminus in Xenopus (3x), it always occurs in this motif. The yeast protein does not display this motif.

The human fibrillarin also contains an approximately 90 amino acid stretch from Glu-133 to Lys-222, a region which bears a striking resemblance to domains which participate in RNA binding interactions. Query et al., supra; Bandziulio et al., supra, Mattaj supra. The domain can be aligned with domains from SnRNP proteins U1A, U1B and U1-70 k, as shown by Lapeyre et al., Mol. Cell Biol. 10: 430–434 (1990). An amino acid sequence 8 units along starting at Gly-185 resembles the octomeric RNP consensus sequence. With the exception of one amino acid, this sequence is conserved, but it does not agree with the consensus sequence to the same degree as other RNA binding proteins. See Query et al., Bandziulis et al., supra.

The foregoing discussion will show that the majority of variation in primary structure is the 70-80 residues at the amino terminal end, where glycines and alanines are present. The disparity with frog and yeast protein undoubtedly has a great deal to do with why DNA probes from the two species did not identify the human clone, and why unconventional modification, as described supra, were necessary to isolate the clone.

Autoimmune diseases frequently arise in connection with immune responses against nucleic acid associated antigens, and, as has been explained, supra, scleroderma is associated with an autoimmune response to human fibrillarin. Via elucidation of the primary structure of the protein, the potential to address cleavage of the 5' externally transcribed spacer (ETS), as well as RNA binding functions at the molecular level, is offered.

The invention describes the isolation of nucleic acid sequences, including cDNA and mRNA which express or encode the human fibrillarin gene. Also described are vectors, such as the plasmid p20J2, which incorporate the nucleic acid therein, and then express it. The isolation of these species puts the genomic-DNA well within the hands of the skilled artisan as well.

It will also be seen that possession of these clones enabled the invention to prepare quantities of the fibrillarin protein using an in vitro expression system. In turn, this led to the isolation and characterization of the human protein.

The purification of the protein allows the skilled artisan to diagnose for scleroderma in a way not possible previously. As has been recognized, supra, the autoimmune condition scleroderma is characterized by antibodies against fibrillarin, but precise diagnosis has not been possible, because the human protein has not been available. The foregoing data show, however, that using the purified protein one can specifically detect the antibodies in mixed samples, such as serum. As such, a diagnostic method is provided where the pure protein is combined with a test serum under conditions which permit reaction of the anti fibrillarin antibodies, and detection of that reaction.

It will also be understood that the nucleic acid sequence expressing human fibrillarin, as with any nucleic acid sequence, is subject to allelic variation, given the known degeneracy of the genetic code. As such, the "nucleic acid sequence" as used herein is not, and should not be interpreted to be limited to the specific sequence shown in sequence id no: 1. Rather, any and all allelic variations which expresses the protein are also embraced herein.

This application also discloses a particular sequence, and the artisan will recognize that such a sequence puts into his or her hands nucleic acid sequences which hybridize with, or are complementary to the disclosed sequence. Given the breadth of these terms, "hybridize" and "complementary" as used herein, refer to nucleic acid sequences which also encode enough of the fibrillarin protein such that those properties of the molecule described herein, such as the ability to identify antifibrillarin antibodies in serum, are possessed by the resulting translation product.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule consisting essentially of a nucleatide sequence found in human genomic DNA encoding fibrillarin.

2. An isolated nucleic acid molecule consisting essentially of cDNA derived from a naturally-occurring human mRNA which codes for fibrillarin.

3. The isolated nucleic acid molecule of claim 2, having the nucleotide sequence of FIG. 1.

4. A recumbinant vector comprising the isolated nucleic acid molecule of claim 1.

5. A recombinant vector comprising the isolated nucleic acid molecule of claim 2.

6. A recombinant vector comprising the isolated nucleic acid molecule of claim 3.

7. An isolated nucleic acid molecule which:

(i) codes for at least a portion of human fibrillarin, (ii) does not hybridize to a nucleic acid molecule coding for NOP1 and 1xSSC at 50° C., and (iii) does not hybridize to a nucleic acid molecule coding for Xomfib at 0.5xSSC and 50° C.

8. An isolated nucleic acid molecule consisting of the open reading frame of the nucleotide sequence of FIG. 1.

9. The isolated nucleic acid molecule of claim 1, wherein said isolated nucleic acid molecule codes for a protein consisting of the amino acid sequence set forth in FIG. 1.

10. The isolated nucleic acid molecule of claim 2, wherein said isolated nucleic acid molecule codes for a protein consisting of the amino acid sequence set forth in FIG. 1.

* * * * *